United States Patent
Crawford (12)

(10) Patent No.: US 10,610,737 B1
(45) Date of Patent: Apr. 7, 2020

(54) SYSTEM AND METHOD FOR USING VIDEO-SYNCHRONIZED ELECTROMYOGRAPHY TO IMPROVE NEUROMUSCULAR PERFORMANCE OF A TARGET MUSCLE

(71) Applicant: Bruce Scott Crawford, Reno, NV (US)

(72) Inventor: Bruce Scott Crawford, Reno, NV (US)

(*) Notice: Subject to any disclaimer, the term of this patent is extended or adjusted under 35 U.S.C. 154(b) by 691 days.

(21) Appl. No.: 14/711,710

(22) Filed: May 13, 2015

Related U.S. Application Data

(63) Continuation-in-part of application No. 13/747,402, filed on Jan. 22, 2013, now abandoned.

(51) Int. Cl.
*A63B 24/00* (2006.01)
*A61B 5/0488* (2006.01)

(52) U.S. Cl.
CPC ........ *A63B 24/0087* (2013.01); *A61B 5/0488* (2013.01); *A63B 2024/0065* (2013.01)

(58) Field of Classification Search
CPC ........ A63B 24/0087; A63B 2024/0065; A61B 5/0488
USPC .......................................................... 434/257
See application file for complete search history.

(56) References Cited

U.S. PATENT DOCUMENTS

| | | | |
|---|---|---|---|
| 8,016,767 B2* | 9/2011 | Miles | A61B 5/0488 600/202 |
| 8,535,224 B2* | 9/2013 | Cusimano Reaston | A61B 5/00 128/920 |
| 2002/0198473 A1* | 12/2002 | Kumar | A61N 1/08 600/595 |
| 2004/0248713 A1* | 12/2004 | Campanaro | A63B 21/068 482/123 |
| 2008/0288020 A1* | 11/2008 | Einav | A61N 1/36003 607/48 |
| 2011/0217683 A1* | 9/2011 | Vlasenko | G09B 19/00 434/257 |
| 2012/0184871 A1* | 7/2012 | Jang | A61B 5/221 600/546 |
| 2012/0253249 A1* | 10/2012 | Wilson | A61N 1/36057 601/154 |
| 2013/0171599 A1* | 7/2013 | Bleich | A61B 5/0456 434/247 |
| 2014/0039340 A1* | 2/2014 | Young | A61B 5/0488 600/546 |
| 2015/0072326 A1* | 3/2015 | Mauri | A61B 5/0488 434/247 |
| 2016/0150993 A1* | 6/2016 | Powell | A61B 5/0488 600/301 |
| 2016/0310069 A1* | 10/2016 | Sinderby | A61B 5/0452 |

(Continued)

*Primary Examiner* — Xuan M Thai
*Assistant Examiner* — Sadaruz Zaman
(74) *Attorney, Agent, or Firm* — Plager Schack LLP; Mark H. Plager; Stephen Hallberg

(57) ABSTRACT

A system and method for using video-synchronized electromyography to improve neuromuscular performance of a target muscle is disclosed. A subject may perform a series of exercises or movements that are candidates for inclusion in an exercise regimen. Video of the subject performing the candidate movements may be combined with electromyogram data from a target muscle and a facilitating muscle. The clips may be analyzed to determine the best exercises for the subject to achieve his or her fitness goals for the target muscle.

9 Claims, 4 Drawing Sheets

(56) References Cited

U.S. PATENT DOCUMENTS

2019/0142339 A1* 5/2019 Thommandram ... A61B 5/4884
600/388

* cited by examiner

SYSTEM AND METHOD FOR USING VIDEO-SYNCHRONIZED ELECTROMYOGRAPHY TO IMPROVE NEUROMUSCULAR PERFORMANCE OF A TARGET MUSCLE

CLAIM OF BENEFIT TO PRIOR APPLICATION

This application is a continuation-in-part of and claims benefit to U.S. Non-Provisional patent application Ser. No. 13/747,402, entitled "SYSTEM AND METHOD FOR USING VIDEO-SYNCHRONIZED ELECTROMYOGRAPHY TO IMPROVE NEUROMUSCULAR PERFORMANCE OF A TARGET MUSCLE," filed Jan. 22, 2013. The U.S. Non-Provisional patent application Ser. No. 13/747,402 is incorporated herein by reference.

BACKGROUND

1. Field of the Present Disclosure

The present disclosure is directed to a system and method for using video-synchronized electromyography to improve neuromuscular performance of a target muscle.

2. Related Art

Exercise programs prescribed for fitness training or rehabilitation often take a "one size fits all" approach without considering individual differences in neuromuscular performance. In fact, different individuals have differing abilities in terms of how well they perform each exercise within a set of exercises.

Personal trainers and physical therapists have long used palpation of muscles to determine whether a given muscle is being activated appropriately. Certain muscles, such as the pelvic floor muscles, are difficult to palpate especially during exercise that involves movement. In addition, certain target muscles, such as the pelvic floor muscles, may be difficult for an individual to voluntarily contract. Additionally, it is commonly observed that some individuals can not perceive if and when a specific target muscle, such as the pelvic floor, is contracted or relaxed. In general, voluntary contraction of a muscle results in only a partial contraction, i.e., contraction of only a fraction of the muscle fibers, in the muscle or muscle group. The potential exists to increase the number of muscle fibers that fire during contraction through a number of different techniques including: resistance training, plyometric exercise, and exercise overflow. The principal of exercise overflow states that exercise of muscles in one area of the body may affect muscle activity in another area of the body. This effect is well documented in the literature and has been used in the rehabilitation of muscular injuries and paralysis associated with cerebral vascular accidents. By contracting a facilitating muscle or muscles to achieve partial engagement of a target muscle and then, while partially engaged, adding a maximal contraction of the target muscle, an individual may more completely contract the target muscle.

The particular movements or exercises that best facilitate contracting the target muscle may vary considerably from one individual to another. For example, it is known that the gluteal muscles, the lower extremity adductors, and the transversus abdominis will all exhibit the principal of exercise overflow on the pelvic floor muscles. The degree to which each of these facilitating muscle groups affects pelvic floor activity varies from individual to individual. To date it has not been possible to take advantage of the principal of exercise overflow in the context of conditioning difficult to monitor muscle groups (such as the pelvic floor).

BRIEF DESCRIPTION

The present disclosure provides systems and methods for determining which movements or exercises best facilitate contracting a target muscle, which results in a significant increase in effectiveness of and compliance with a prescribed exercise regimen, as well as other advantages apparent from the discussion herein. For example, described herein is a method of monitoring both facilitating and target muscles during movements that naturally engage the facilitating muscles. The method involves analysis of the quantity of facilitated target muscle activity as well as the cumulative effect of facilitation plus voluntary target muscle activation associated with various different exercises so as to identify those exercises that are most ideal for a given individual.

According to one aspect of the present disclosure, a method for using video-synchronized electromyography to improve the neuromuscular performance of a target muscle includes selecting two or more candidate movements. Each candidate movement may facilitate engagement of a target muscle. The method also includes recording two or more synchronized clips. A synchronized clip includes a first electromyogram (EMG) of a target muscle, a second EMG of a facilitating muscle, and a video of a subject performing a candidate movement. The first EMG and the second EMG are synchronized with the video. The video data is used to confirm that the EMG signals from the first and second muscle groups are engaged at the appropriate moments during each movement. The method further includes analyzing the synchronized clips and selecting the candidate movements that provide facilitation of the target muscle.

According to another aspect of the present disclosure, a system for using video-synchronized electromyography to improve the neuromuscular performance of a target muscle includes a video camera, a first electromyograph, a second electromyograph, and a computer. The video camera is configured to transmit video of a subject performing a candidate movement. The first electromyograph is configured to record a first EMG of a target muscle while the subject performs the candidate movement. The second electromyograph is configured to record a second EMG of a facilitating muscle while the subject performs the candidate movement. The computer is configured to synchronize the video from the video camera, the first EMG, and the second EMG, thereby producing a synchronized clip.

Additional features, advantages, and aspects of the present disclosure may be set forth or apparent from consideration of the following detailed description, drawings, and claims. Moreover, it is to be understood that both the foregoing summary of the present disclosure and the following detailed description are exemplary and intended to provide further explanation without limiting the scope of the present disclosure as claimed.

BRIEF DESCRIPTION OF THE DRAWINGS

The accompanying drawings, which are included to provide a further understanding of the present disclosure, are incorporated in and constitute a part of this specification, illustrate aspects of the present disclosure and together with the detailed description serve to explain the principles of the present disclosure. No attempt is made to show structural details of the present disclosure in more detail than may be necessary for a fundamental understanding of the present disclosure and the various ways in which it may be practiced. In the drawings.

DETAILED DESCRIPTION

Figure 1:
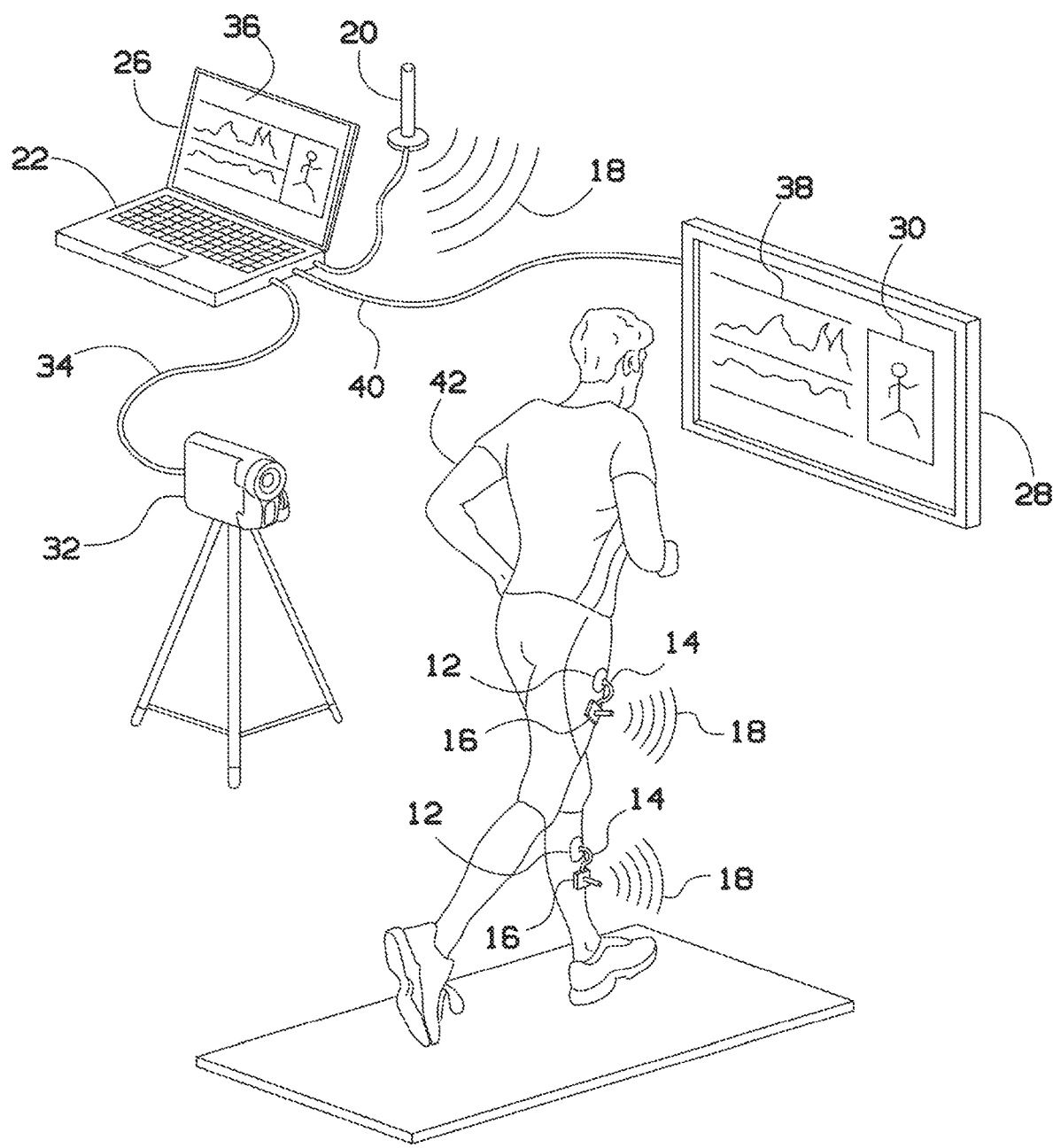
FIG. 1 shows an exemplary system for recording a synchronized video and electromyogram clip, according to an aspect of the present disclosure.

The aspects of the present disclosure and the various features and advantageous details thereof are explained more fully with reference to the non-limiting aspects and examples that are described and/or illustrated in the accompanying drawings and detailed in the following description. It should be noted that the features illustrated in the drawings are not necessarily drawn to scale, and features of one aspect may be employed with other aspects as the skilled artisan would recognize, even if not explicitly stated herein. Descriptions of well-known components and processing techniques may be omitted so as to not unnecessarily obscure the aspects of the present disclosure. The examples used herein are intended merely to facilitate an understanding of ways in which the present disclosure may be practiced and to further enable those of skill in the art to practice the aspects of the present disclosure. Accordingly, the examples and aspects herein should not be construed as limiting the scope of the present disclosure, which is defined solely by the appended claims and applicable law. Moreover, it is noted that like reference numerals represent similar parts throughout the drawings.

FIG. 1 shows an exemplary system for recording a synchronized video and electromyogram (EMG) clip, according to an aspect of the present disclosure. The system may include one or more electromyographs, and each electromyograph may include a surface electrode 12 and electrode wires 14. Each electrode 12 may be placed on a body surface of a subject 42 being monitored. Each electrode 12 may be connected to a wireless transmitter 16 or wired to a data collection device, such as a computer 22. In a wireless system, the computer 22 may be equipped with an antenna 20 to receive wireless signals 18 from the wireless transmitters 16.

The system may also include a video camera 32 that may record or transmit video of the subject 42 performing one or more exercises. The video camera 32 may be connected to the computer 22 by a video cable 34 or a wireless connection and the computer 22 may receive video from the video camera 32. The computer may be configured to synchronize the display of the video and the EMG data, producing a synchronized clip 36. The synchronization may take place in real time, so that the computer may be configured to display a live video feed 30 with synchronized EMG data 38. The synchronized clip 36 may be displayed on a display device connected to the computer 22, including, e.g., a computer screen 26 and a monitor 28 connected to the computer 22. The monitor 28 may be connected to the computer 22 with a monitor cable or a wireless connection.

Figure 2:
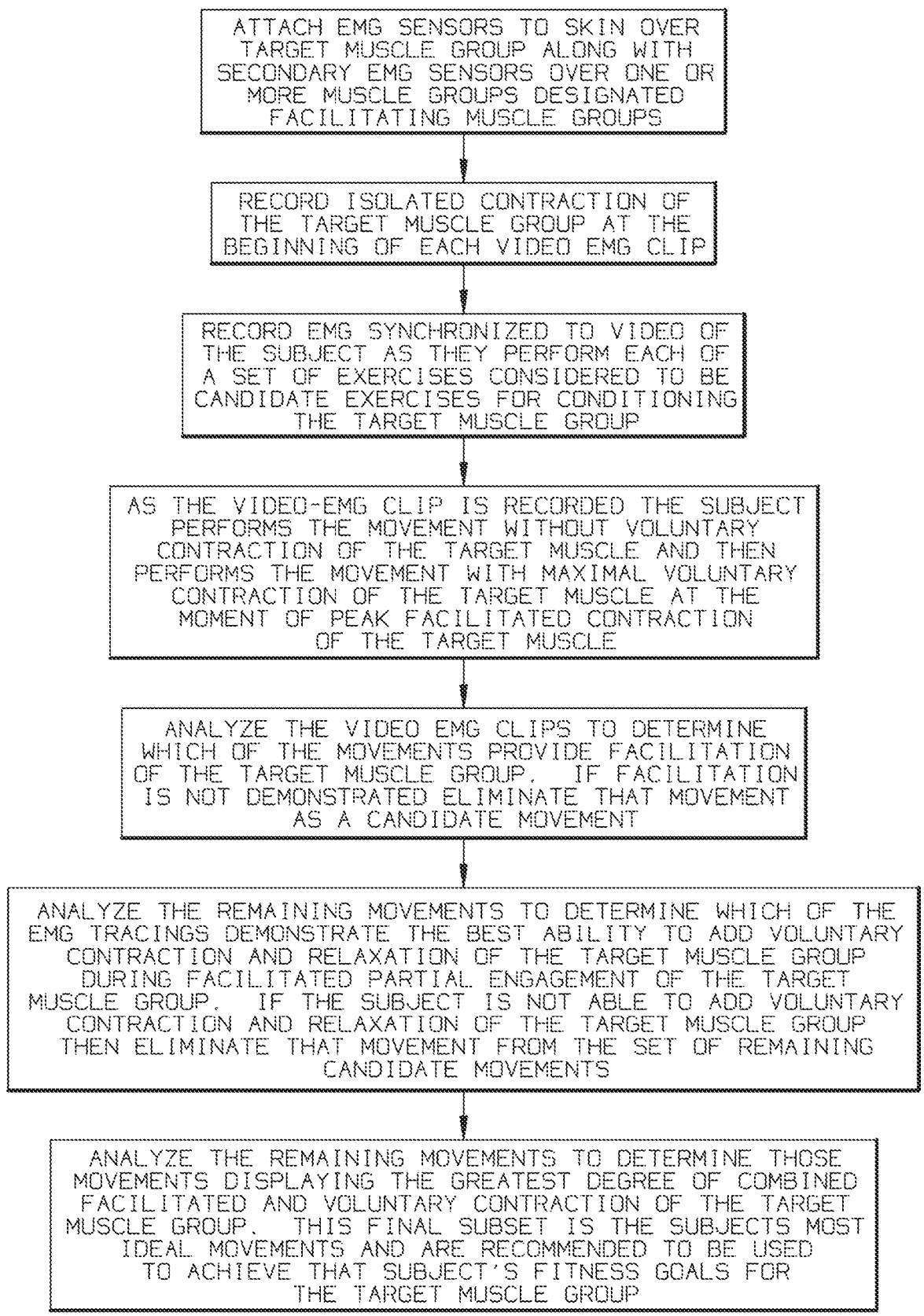
FIG. 2 shows a flowchart for recording and analyzing a synchronized video and electromyogram clip, according to an aspect of the present disclosure.

FIG. 2 shows a flowchart for recording and analyzing a synchronized video and electromyogram clip, according to an aspect of the present disclosure. One electrode 12 may be placed over a target muscle that needs to be exercised or strengthened. One or more additional electrodes may be placed over other muscles, referred to as facilitating muscles, that may facilitate contraction of the target muscles. To develop a customized training program, the subject 42 may be asked to perform a series of exercises or movements that are candidates for inclusion in the training program. The system may be used to produce one or more synchronized clips 36 for each candidate movement. At the beginning of each clip 36, the subject is asked to perform a maximal isolated voluntary contraction of the target muscle so as to determine the degree to which the use of facilitation plus voluntary contraction increases the activation of the target muscle beyond that achieved with a maximal isolated contraction alone.

The synchronized clips 36 may be analyzed to determine which of the candidate movements provides facilitation of the target muscle. Facilitation or facilitated engagement means partial engagement of the target muscle due to voluntary contraction of a facilitating muscle. Any movement that does not provide facilitation may be removed from the list of candidate movements. The clips 36 of the remaining movement may be analyzed to determine which movements provide the greatest degree of target muscle activity when a maximal voluntary contraction of the target muscle is added to the facilitated contraction achieved by the movement being tested. Movements in which the subject is not able to add additional voluntary target muscle activation may be removed from the list of candidate movements. The clips 36 of the remaining movements may be further analyzed to determine the movements that display the greatest degree of combined facilitated and voluntary contraction of the target muscle. This final subset may be the subject's most ideal movements for exercising or strengthening the target muscle and may be recommended to be used to achieve the subject's fitness goals for the target muscle.

Individuals differ in neuromuscular performance and how well they perform each exercise within a set of exercises. Selecting only the movements that an individual performs best can produce a customized program for that individual, which may be more efficient and/or effective than a standardized program applied to each individual without accounting for differences in ability and performance. Other systems do not make use of analysis of facilitated engagement of one muscle group by voluntary use of a second muscle group. Other systems do not use synchronized video and EMG data in a process of filtering or removing movements from a set of candidate movements to create a subset of most ideal movements for an individual. By creating a subset of exercises that are demonstrated to be a subject's most ideal movements, a substantial majority of the subjects efforts may be applied most efficiently and goals may be more readily realized. With more rapid attainment of fitness goals, compliance with a recommended exercise regimen may be greater.

Figure 3:
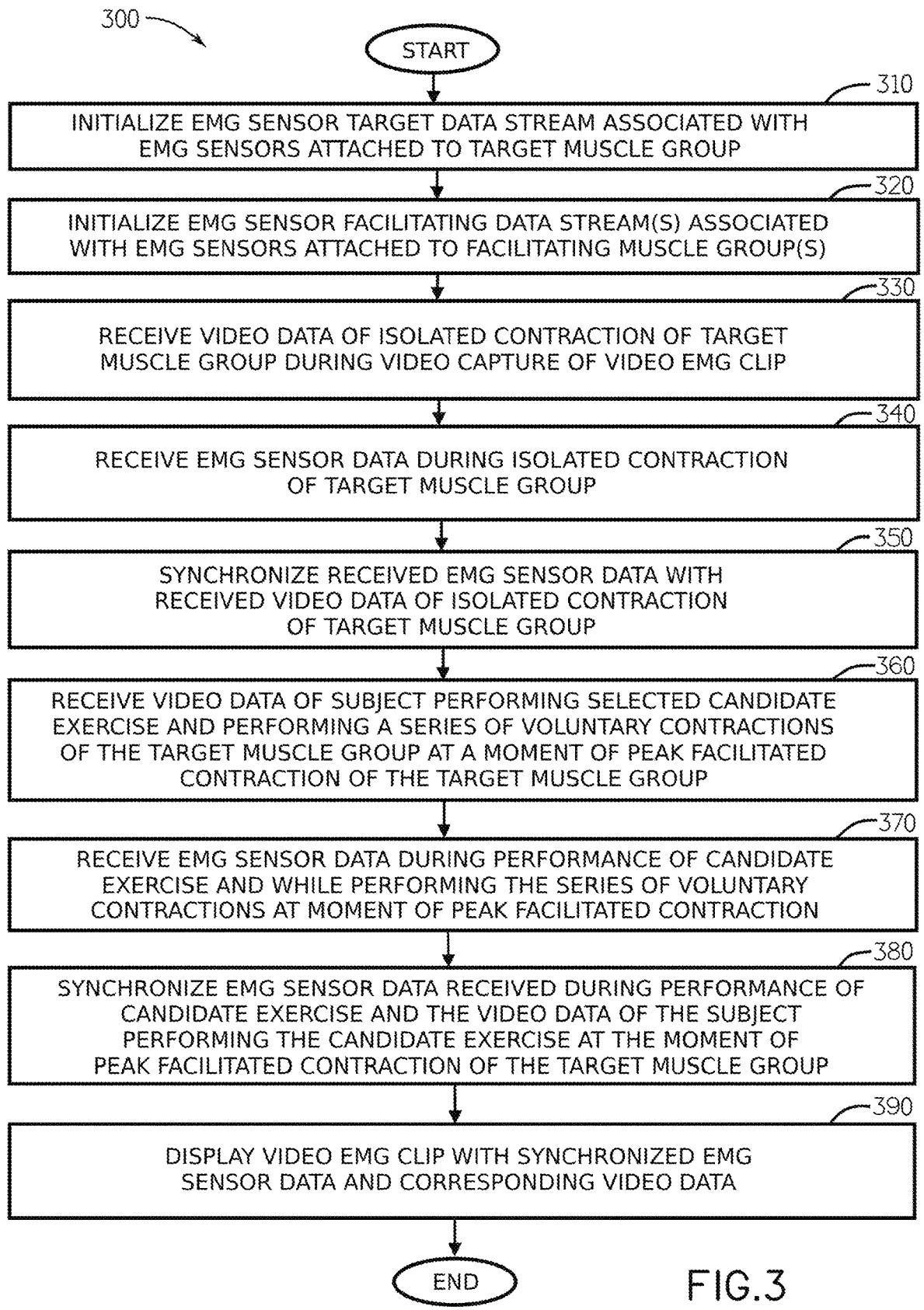
FIG. 3 conceptually illustrates a process for receiving video and electromyogram sensor data and generating a composite synchronized video with overlaying graphs of the electromyogram sensor data in some embodiments.

By way of example, FIG. 3 conceptually illustrates a process 300 for receiving video and electromyogram sensor data and generating a composite synchronized video with overlaying graphs of the electromyogram sensor data. The process 300 of some embodiments is implemented as a software application that runs on a processor of a computing device, such as the computer 22 described above by reference to FIG. 1. The process 300, therefore, may be performed by the computing device when the processor of the computing device is configured to perform instructions of the software application. While reference is made to the computer 22 of the exemplary system for recording a synchronized video and EMG clip, described above according to FIG. 1, a person skilled in the relevant art would appreciate that any of several computing devices with sufficient hardware resources could be used to perform the steps of the process 300. Further examples of computing devices, electronic systems, and other such devices are described below by reference to FIG. 4.

In some embodiments, the process 300 starts when a user identifies a set of candidate exercises for a subject to perform with EMG sensors placed on the subject's body surface area (e.g., skin) proximate to the target muscle group and one or more facilitating muscle groups. For example, the user may identify a first candidate exercise movement for the subject to perform in relation to contraction, if any, of a target muscle and a facilitating muscle, and a different second candidate exercise movement for the subject to perform in relation to contraction, if any, of the same target muscle and the same facilitating muscle. Once the candidate exercises are identified, a video EMG clip is recorded while the subject performs an isolated contraction of target muscle group. For instance, if the target muscle group is the pelvic floor muscle group, the subject will perform an isolated contraction of the pelvic floor that is captured in the video EMG clip. After the isolated contraction of the target muscle group, the subject performs one of the candidate exercises (e.g., the first candidate exercise), which is also recorded in the video EMG clip. At some point during performance of the candidate exercise, the target muscle group reaches peak facilitated engagement. When peak facilitated engagement occurs, the subject then adds a series of voluntary contractions of the target muscle group. With each voluntary contraction, the subject may forcefully exhale (e.g., with mouth open) to enhance engagement of one or more facilitating muscles. All of the voluntary contractions of the target muscle group are performed during the candidate exercise movement, and so, are included in the video EMG clip. Also, while the process 300 starts with one of the candidate exercises (e.g., the first candidate exercise), the process 300 would be repeated for each candidate exercise in order for the user and/or subject to perform a meaningful comparison and identify the best exercises.

With a candidate exercise selected, the process 300 initializes (at 310) a target muscle EMG data input stream for EMG sensor data to be received from the EMG sensors attached to the subject at the target muscle group. Next, the process 300 initializes (at 320) a set of facilitating muscle EMG data input streams for EMG sensor data to be received from EMG sensors attached to the subject at one or more facilitating muscle groups.

After the EMG sensor data streams are initialized, the process 300 of some embodiments receives (at 330) video data of the subject performing isolated contraction of the target muscle group. This isolated contraction of the target muscle group is performed before the subject performs the selected candidate exercise. In some embodiments, the video data is received as a stream of video data associated with the video EMG clip as captured by a video camera device.

Contemporaneously with receiving the video data (at 330), the process 300 of some embodiments receives (at 340) EMG sensor data associated with the target muscle group and the facilitating muscle group(s). The received EMG sensor data is associated with the isolated contraction of the target muscle group. In some embodiments, the process 300 synchronizes (at 350) the isolated target muscle group contraction video and the received EMG sensor data.

Next, the process 300 of some embodiments receives (at 360) video data of the subject performing the selected candidate exercise. A moment is reached during performance of the candidate exercise at which the subject performs a series of voluntary contractions of the target muscle group while forcefully exhaling to engage facilitating muscles. This moment is peak facilitated contraction of the target muscle group. Also, the video data is received in some embodiments in the ongoing stream of video data associated with the video EMG clip.

Contemporaneously with receiving the ongoing stream of video data (at 360), the process 300 of some embodiments receives (at 370) EMG sensor data associated with the target muscle group and the facilitating muscle group(s). The received EMG sensor data is associated with the candidate exercise performed when the subject performs the series of voluntary contractions of the target muscle group and when forcefully exhaling air to engage facilitating muscles (i.e., the moment of peak facilitated contraction of the target muscle group). In some embodiments, the process 300 then synchronizes (at 380) video data during performance of the candidate exercise with the received EMG sensor data.

While the process 300 of some embodiments displays the video EMG clip in real-time (i.e., as the video and EMG data is recorded and received), in some cases, the process 300 generates (at 390) a composite video that includes (i) the video EMG clip and (ii) graphical data quantifying the EMG sensor data. After real-time streaming of the video EMG clip or generation of the composite video for playback, the process 300 of some embodiments ends.

As noted above, if there are multiple candidate exercises to evaluate, the process 300 is repeated for each candidate exercise selected by the user, and a separate video EMG clip is recorded in relation to the candidate exercise. This allows the user or subject to compare the candidate exercises. After analyzing the video EMG clips for each candidate exercise, the user and/or the subject can then identify specific exercises among the candidate exercises which are not useful for facilitating target muscle contraction and those which are highly efficient at facilitating target muscle contraction. As described above by reference to FIG. 2, the user and/or subject can then identify one or more exercises in ways that are not perceptible to a subject performing an exercise, or which are not sufficiently noticeable to the subject in order to identify one or more exercises focused on a specific target muscle group.

While the present disclosure has been described in terms of exemplary aspects, those skilled in the art will recognize that the present disclosure can be practiced with modifications in the spirit and scope of the appended claims. These examples given above are merely illustrative and are not meant to be an exhaustive list of all possible designs, aspects, applications or modifications of the present disclosure.

Many of the above-described features and applications are implemented as software processes that are specified as a set of instructions recorded on a computer readable storage medium (also referred to as computer readable medium or machine readable medium). When these instructions are executed by one or more processing unit(s) (e.g., one or more processors, cores of processors, or other processing units), they cause the processing unit(s) to perform the actions indicated in the instructions. Examples of computer readable media include, but are not limited to, CD-ROMs, flash drives, RAM chips, hard drives, EPROMs, etc. The computer readable media does not include carrier waves and electronic signals passing wirelessly or over wired connections.

In this specification, the term "software" is meant to include firmware residing in read-only memory or applications stored in magnetic storage, which can be read into memory for processing by a processor. Also, in some embodiments, multiple software inventions can be implemented as sub-parts of a larger program while remaining distinct software inventions. In some embodiments, multiple software inventions can also be implemented as separate programs. Finally, any combination of separate programs that together implement a software invention described here is within the scope of the invention. In some embodiments, the software programs, when installed to operate on one or more electronic systems, define one or more specific machine implementations that execute and perform the operations of the software programs.

Figure 4:
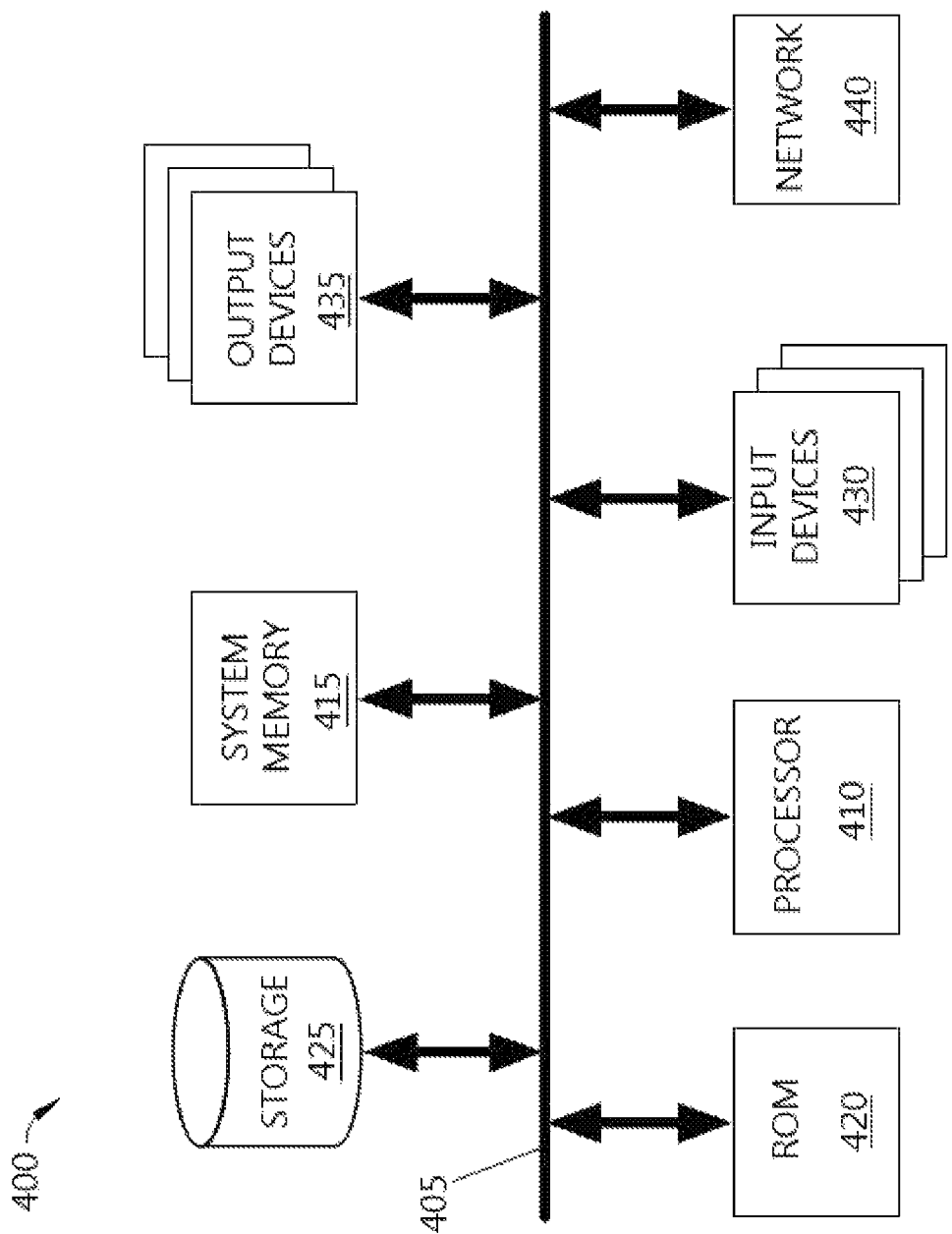
FIG. 4 conceptually illustrates an electronic system with which some embodiments of the invention are implemented.

FIG. 4 conceptually illustrates an electronic system 400 with which some embodiments of the invention are implemented. The electronic system 400 may be a computer, phone, PDA, or any other sort of electronic device. Such an electronic system includes various types of computer readable media and interfaces for various other types of computer readable media. Electronic system 400 includes a bus 405, processing unit(s) 410, a system memory 415, a read-only 420, a permanent storage device 425, input devices 430, output devices 435, and a network 440.

The bus 405 collectively represents all system, peripheral, and chipset buses that communicatively connect the numerous internal devices of the electronic system 400. For instance, the bus 405 communicatively connects the processing unit(s) 410 with the read-only 420, the system memory 415, and the permanent storage device 425.

From these various memory units, the processing unit(s) 410 retrieves instructions to execute and data to process in order to execute the processes of the invention. The processing unit(s) may be a single processor or a multi-core processor in different embodiments.

The read-only-memory (ROM) 420 stores static data and instructions that are needed by the processing unit(s) 410 and other modules of the electronic system. The permanent storage device 425, on the other hand, is a read-and-write memory device. This device is a non-volatile memory unit that stores instructions and data even when the electronic system 400 is off. Some embodiments of the invention use a mass-storage device (such as a magnetic or optical disk and its corresponding disk drive) as the permanent storage device 425.

Other embodiments use a removable storage device (such as a floppy disk or a flash drive) as the permanent storage device 425. Like the permanent storage device 425, the system memory 415 is a read-and-write memory device. However, unlike storage device 425, the system memory 415 is a volatile read-and-write memory, such as a random access memory. The system memory 415 stores some of the instructions and data that the processor needs at runtime. In some embodiments, the invention's processes are stored in the system memory 415, the permanent storage device 425, and/or the read-only 420. For example, the various memory units include instructions for processing appearance alterations of displayable characters in accordance with some embodiments. From these various memory units, the processing unit(s) 410 retrieves instructions to execute and data to process in order to execute the processes of some embodiments.

The bus 405 also connects to the input and output devices 430 and 435. The input devices enable the user to communicate information and select commands to the electronic system. The input devices 430 include alphanumeric keyboards and pointing devices (also called "cursor control devices"). The output devices 435 display images generated by the electronic system 400. The output devices 435 include printers and display devices, such as cathode ray tubes (CRT) or liquid crystal displays (LCD). Some embodiments include devices such as a touchscreen that functions as both input and output devices.

Finally, as shown in FIG. 4, bus 405 also couples electronic system 400 to a network 440 through a network adapter (not shown). In this manner, the computer can be a part of a network of computers (such as a local area network ("LAN"), a wide area network ("WAN"), or an intranet), or a network of networks (such as the Internet). Any or all components of electronic system 400 may be used in conjunction with the invention.

These functions described above can be implemented in digital electronic circuitry, in computer software, firmware or hardware. The techniques can be implemented using one or more computer program products. Programmable processors and computers can be packaged or included in mobile devices. The processes may be performed by one or more programmable processors and by one or more set of programmable logic circuitry. General and special purpose computing and storage devices can be interconnected through communication networks.

Some embodiments include electronic components, such as microprocessors, storage and memory that store computer program instructions in a machine-readable or computer-readable medium (alternatively referred to as computer-readable storage media, machine-readable media, or machine-readable storage media). Some examples of such computer-readable media include RAM, ROM, read-only compact discs (CD-ROM), recordable compact discs (CD-R), rewritable compact discs (CD-RW), read-only digital versatile discs (e.g., DVD-ROM, dual-layer DVD-ROM), a variety of recordable/rewritable DVDs (e.g., DVD-RAM, DVD-RW, DVD+RW, etc.), flash memory (e.g., SD cards, mini-SD cards, micro-SD cards, etc.), magnetic and/or solid state hard drives, read-only and recordable Blu-Ray® discs, ultra density optical discs, any other optical or magnetic media, and floppy disks. The computer-readable media may store a computer program that is executable by at least one processing unit and includes sets of instructions for performing various operations. Examples of computer programs or computer code include machine code, such as is produced by a compiler, and files including higher-level code that are executed by a computer, an electronic component, or a microprocessor using an interpreter.

While the invention has been described with reference to numerous specific details, one of ordinary skill in the art will recognize that the invention can be embodied in other specific forms without departing from the spirit of the invention. For instance, FIGS. 2 and 3 conceptually illustrate processes. The specific operations of each process may not be performed in the exact order shown and described. Specific operations may not be performed in one continuous series of operations, and different specific operations may be performed in different embodiments. Furthermore, each process could be implemented using several sub-processes, or as part of a larger macro process. Thus, one of ordinary skill in the art would understand that the invention is not to be limited by the foregoing illustrative details, but rather is to be defined by the appended claims.

I claim:

1. A system for using video-synchronized electromyography to improve neuromuscular performance of a target muscle, the system comprising:
   a video camera configured to capture and transmit a set of videos of a subject performing a set of candidate body movements;
   a first electromyograph configured to record, for each candidate body movement, a first set of electromyograms (EMG) of a target muscle, said first set of EMGs comprising a baseline EMG while the subject performs an isolated voluntary contraction of the target muscle and a first EMG of the target muscle while the subject performs the candidate body movement;
   a second electromyograph configured to record, for each candidate body movement, a second set of EMGs of a set of facilitating muscles, said second set of EMGs comprising a second EMG of each facilitating muscle in the set of facilitating muscles while the subject performs the candidate body movement; and
   a computer configured to perform a plurality of operations that identify candidate body movements that improve neuromuscular performance of the target muscle and visually output a composite video stream of the EMGs overlaying the set of videos, said plurality of operations comprising:
      receiving the set of videos, the first set of EMGs for each candidate body movement, and the second set of EMGs for each candidate body movement;
      synchronizing, for each candidate body movement, the video from the video camera, the first set of EMGs, and the second set of EMGs;
      generating, for each candidate body movement, the composite video stream from a combination of the synchronized video, the first set of EMGs, and the second set of EMGs; and
      displaying the composite video stream contemporaneously with the subject performing the associated candidate body movement.

2. The system of claim 1, further comprising:
   a first wireless transmitter associated with the first electromyograph, said first wireless transmitter for transmitting the first set of EMGs to the computer;
   a set of second wireless transmitters associated with the set of second electromyographs, said set of second wireless transmitters for transmitting the second set of EMGs to the computer; and
   a wireless antenna associated with the computer, the wireless antenna configured to facilitate wireless communication between the computer and each electromyograph.

3. The system of claim 1, wherein the computer is further configured to perform a set of operations for displaying each composite video stream on a plurality of display screens in near real time as the candidate body movements are performed.

4. The system of claim 3, wherein at least one of the display screens is a computer screen.

5. The system of claim 1, wherein at least one of the display screens is a monitor configured to connect to the computer.

6. A non-transitory computer readable medium storing a program which, when executed by a processor of a computing device, generates a composite synchronized video of an electromyogram (EMG) clip and a clip of a subject performing an exercise, said program comprising sets of instructions for:
   receiving, by the computing device, contraction video data captured by a video camera of an isolated contraction of a target muscle group by a subject;
   receiving, by the computing device, contraction EMG data captured by an EMG sensor as the subject performs the isolated contraction of the target muscle group;
   synchronizing, by the computing device, timing of the contraction EMG data and the contraction video data;
   receiving, by the computing device, candidate exercise video data captured by the video camera while the subject performs a selected candidate exercise and a series of voluntary contractions of the target muscle group at a moment of peak facilitated contraction of the target muscle group;
   receiving, by the computing device, candidate exercise EMG data captured by the EMG sensor while the subject performs the selected candidate exercise and the series of voluntary contractions of the target muscle group at the moment of peak facilitated contraction of the target muscle group; and
   synchronizing, by the computing device, the candidate exercise EMG data and the candidate exercise video data.

7. The non-transitory computer readable medium of claim 6, wherein the contraction EMG data and the contraction video data are synchronized contemporaneously with receiving the contraction EMG data and the contraction video data.

8. The non-transitory computer readable medium of claim 6, wherein the candidate exercise EMG data and the candidate exercise video data are synchronized contemporaneously with receiving the candidate exercise EMG data and the candidate exercise video data.

9. The non-transitory computer readable medium of claim 6, wherein the program further comprises sets of instructions for:
   generating a composite video stream from the synchronized combination of the candidate exercise EMG data and the candidate exercise video data; and
   visually outputting the generated composite video stream on at least one video monitor for at least one of a patient and a medical professional to view in real time as the patient performs the body movements.

* * * * *